US006494920B1

(12) United States Patent
Weuthen et al.

(10) Patent No.: US 6,494,920 B1
(45) Date of Patent: Dec. 17, 2002

(54) DETERGENT MIXTURES

(75) Inventors: Manfred Weuthen, Langenfeld (DE); Rafael Pi Subirana, Granollers (ES); José Blasquez Fernandez, Terrassa (ES); Bernd Fabry, Korschenbroich (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/890,693

(22) PCT Filed: Jan. 25, 2000

(86) PCT No.: PCT/EP00/00531
§ 371 (c)(1),
(2), (4) Date: Nov. 2, 2001

(87) PCT Pub. No.: WO00/45788
PCT Pub. Date: Aug. 10, 2000

(30) Foreign Application Priority Data

Feb. 4, 1999 (DE) ......................... 199 04 513

(51) Int. Cl.$^7$ ........................... C11D 1/62; C11D 3/382; A61K 7/06; A61K 7/50
(52) U.S. Cl. ........................... 8/137; 510/123; 510/124; 510/130; 510/158; 510/159; 510/322; 510/327; 510/329; 510/330; 510/504; 424/70.28; 134/42
(58) Field of Search ................. 510/123, 124, 510/130, 158, 159, 322, 327, 329, 330, 504; 424/70.28; 8/137; 134/42

(56) References Cited

U.S. PATENT DOCUMENTS

| | | | |
|---|---|---|---|
| 3,966,629 A | 6/1976 | Dumbrell | 252/140 |
| 4,062,647 A | 12/1977 | Storm et al. | 8/137 |
| 4,172,887 A | 10/1979 | Vanlerberghe et al. | 424/70 |
| 4,602,648 A * | 7/1986 | Syed et al. | 132/7 |
| 4,737,306 A | 4/1988 | Wichelhaus et al. | 252/95 |
| 4,816,553 A | 3/1989 | Baur et al. | 528/245 |
| 4,820,439 A | 4/1989 | Rieck | 252/135 |
| 4,919,846 A | 4/1990 | Nakama et al. | 252/542 |
| 5,008,032 A | 4/1991 | Diessel et al. | 252/174.24 |
| 5,417,951 A | 5/1995 | Just | 423/334 |
| 5,580,941 A | 12/1996 | Krause et al. | 527/300 |
| 5,705,169 A | 1/1998 | Stein et al. | 424/401 |
| 5,718,891 A | 2/1998 | Prat et al. | 424/70.28 |
| 5,730,960 A | 3/1998 | Stein et al. | 424/59 |
| 5,830,956 A | 11/1998 | Stockhausen et al. | 526/318.2 |
| 6,193,960 B1 | 2/2001 | Metzger et al. | 424/59 |

FOREIGN PATENT DOCUMENTS

| | | |
|---|---|---|
| DE | 1 165 574 | 3/1964 |
| DE | 2 024 051 | 12/1971 |
| DE | 2 334 899 | 1/1974 |
| DE | 35 26 405 | 2/1987 |
| DE | 42 21 381 | 2/1994 |
| DE | 43 08 794 | 4/1994 |
| DE | 43 00 772 | 3/1997 |
| DE | 197 30 649 | 9/1998 |
| EP | 0 028 432 | 1/1984 |
| EP | 0 164 514 | 6/1989 |
| EP | 0 280 223 | 10/1991 |
| EP | 0 026 529 | 8/1992 |
| EP | 0 367 049 | 2/1994 |
| EP | 0 786 250 | 7/1997 |
| EP | 0 693 471 | 1/1998 |
| EP | 0 694 521 | 1/1998 |
| EP | 0 818 450 | 1/1998 |
| FR | 2 252 840 | 11/1974 |
| GB | 962919 | 7/1964 |
| GB | 1333475 | 10/1973 |
| GB | 1 400 898 | 7/1975 |
| JP | 59 016813 | 1/1984 |
| WO | WO 91/01295 | 2/1991 |
| WO | WO 91/08171 | 6/1991 |

OTHER PUBLICATIONS

Patent Abstracts of Japan, vol. 008, No. 102, of JP 59 016813, (Jan. 28, 1984).
Puchta et al., "A New Generation of Softeners," Tenside Surf. Det., vol. 30, pp. 186–191, Carl Hanser Verlag, Munich, 1993 No Month Given.
Brock, M., "Neue Entwicklungen auf dem Gebiet der Wäscheweichspüler," Tenside Surf. Det., vol. 30, pp. 394–399, Carl Hanser Verlag, Munich, 1993 No Month Given Not translated.
Lagerman et al., "Synthesis and Performance of Ester Quaternary Biodegradable Softeners," J. Am. Oil. Chem. Soc., vol. 71, pp. 97–100, Jan. 1994.
Shapiro, et al., "Environmentally Friendly Ester Quats," Cosm. Toil., vol. 109, pp. 77, 78, 80, (Dec. 1994).
Lutomski, J, "Aloe, Topizierphanze mit Therapeutischer Wirkung," Pharmaie in unserer Zeit, vol. 13, pp. 172–176, Verlag Chemie GmbH, Weinheim, 1984 No Month Given Not translated.
J. Falbe, et al., "Surfactants in Consumer Products", Springer Verlag, pp. 54 to 125, Berlin, 1987 No Month Given.
J. Falbe, et al., "Katalysatoren, Tenside und Mineralöladditive (Catalysts, Surfactants and Mineral Oil Additives)", Thieme Verlag, pp. 123–217, Stuttgart, 1978 No Month Given Not translated.
Todd et al., "Volatile Silicone Fluids for Cosmetic Formulations," Cosm. Toil., vol. 91, pp. 29–32, (Jan. 1976).
Tronnier et al., "Experimentelle Untersuchungen zur Wirkungsweise Aluminiumhaltiger Antiperspiranzien," J. Soc. Cosm. Chem., vol. 24, p 281–290, 1973 No Month Given Not translated.

(List continued on next page.)

Primary Examiner—Gregory Delcotto
Assistant Examiner—Brian P. Mruk
(74) Attorney, Agent, or Firm—John E. Drach; Steven J. Trzaska

(57) ABSTRACT

A cleaning composition for use in cleaning textile, hair and skin, the composition containing: (a) an esterquat; and (b) aloe.

16 Claims, No Drawings

OTHER PUBLICATIONS

Graham et al., "Inhibition of the Mitochondrial Oxidation of Octanoate by Salicyclic Acid and Related Compounds," J. Pharm. Pharmac, vol. 26, p. 531–534, Hoeschst AG, Frankfurt 1975, No Month Given.

Lochhead et al., "Encyclopedia of Polymers and Thickeners for Cosmetics," Cosm. Toil., vol. 108, pp. 95–135, Allured Publishing Corp., (May 1993).

Finkel, P., "Formulierung Kosmetischer Sonnenschutzmittel," SÖFW–Journal, vol. 122, pp. 543–548, Mar. 1996 Not translated.

"Kosmetische Färbemittel," Farbstoffkommission der Deutschen Forschungsgemeinschaft, Verlag Chemie, Weinheim, pp. 81–106, 1984 No Month Given Not translated.

* cited by examiner

DETERGENT MIXTURES

BACKGROUND OF THE INVENTION

This invention relates to detergent mixtures containing esterquats and aloe and to the use of the mixtures for the production of surface-active compositions.

Numerous surfactant mixtures used in various fields are known from the prior art. In the field of detergent raw materials and cosmetics, however, there is a common demand for concentrated surfactant premixes distinguished by good cleaning and softening properties with respect on the one hand to synthetic fibers, i.e. textiles and their precursors, and on the other hand to natural (keratin) fibers, i.e. human hair. Another requirement the products are expected to satisfy is optimal dermatological compatibility so that there is virtually no risk of even particularly sensitive consumers suffering irritation of the skin either by direct contact with the products or by indirect contact via the treated fibers.

Accordingly, the complex problem addressed by the present invention was to provide new detergent mixtures both for the detergent industry and for the cosmetics industry which would be distinguished by particularly high dermatological compatibility, by favorable skin and textile cleaning and rewetting performance and by excellent softening properties for synthetic and natural fibers.

DESCRIPTION OF THE INVENTION

The present invention relates to detergent mixtures containing (a) esterquats and (b) aloe.

It has surprisingly been found that the detergent mixtures according to the invention not only have particularly good dermatological compatibility, they also have particularly high cleaning performance both for textiles and for the skin and hair. In addition, not only do they provide textiles and hair with a pleasant soft feel, they also reduce the static charging between the fibers. The mixtures are particularly suitable for the production of softeners and skin-care and hair-care products.

Esterquats

"Esterquats" (component a) are generally understood to be quaternized fatty acid triethanolamine ester salts. They are known compounds which may be obtained by the relevant methods of preparative organic chemistry, cf. International patent application WO 91/01295 ((Henkel), in which triethanolamine is partly esterified with fatty acids in the presence of hypophosphorous acid, air is passed through the reaction mixture and the whole is then quaternized with dimethyl sulfate or ethylene oxide. Overviews of this subject have been published, for example, by R. Puchta et al. in Tens. Surf. Det., 30, 186 (1993), by M. Brock in Tens. Surf. Det., 30, 394 (1993), by R. Lagerman et al. in J. Am. Oil Chem. Soc., 71, 97 (1994) and by I. Shapiro in Cosm. Toil. 109, 77 (1994). The quaternized fatty acid triethanolamine ester salts correspond to formula (I):

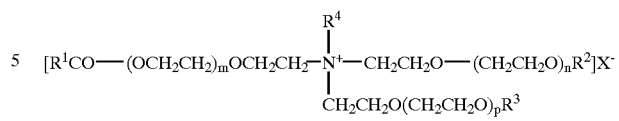

in which $R^1CO$ is an acyl group containing 6 to 22 carbon atoms, $R^2$ and $R^3$ independently of one another represent hydrogen or have the same meaning as $R^1CO$, $R^4$ is an alkyl group containing 1 to 4 carbon atoms or a $(CH_2CH_2O)_qH$ group, m, n and p together stand for 0 or numbers of 1 to 12, q is a number of 1 to 12 and X is halide, alkyl sulfate or alkyl phosphate. Typical examples of esterquats which may be used in accordance with the present invention are products based on caproic acid, caprylic acid, capric acid, lauric acid, myristic acid, palmitic acid, isostearic acid, stearic acid, oleic acid, elaidic acid, arachic acid, behenic acid and erucic acid and the technical mixtures thereof obtained, for example, in the pressure hydrolysis of natural fats and oils. Technical $C_{12/18}$ cocofatty acids and, in particular, partly hydrogenated $C_{16/18}$ tallow or palm oil fatty acids and $C_{16/18}$ fatty acid cuts rich in elaidic acid are preferably used. To produce the quaternized esters, the fatty acids and the triethanolamine may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9 and are derived from technical $C_{16/18}$ tallow or palm oil fatty acid (iodine value 0 to 40). In performance terms, quaternized fatty acid triethanolamine ester salts corresponding to formula (I), in which $R^1CO$ is an acyl group containing 16 to 18 carbon atoms, $R^2$ has the same meaning as $R^1CO$, $R^3$ is hydrogen, $R^4$ is a methyl group, m, n and p stand for 0 and X stands for methyl sulfate, have proved to be particularly advantageous.

Besides the quaternized fatty acid triethanolamine ester salts, other suitable esterquats are quaternized ester salts of fatty acids with diethanolalkyamines corresponding to formula (II):

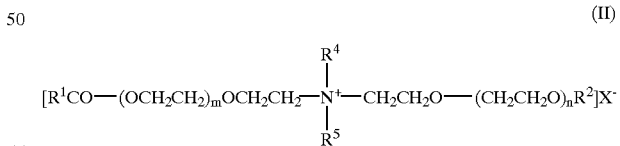

in which $R^1CO$ is an acyl group containing 6 to 22 carbon atoms, $R^2$ is hydrogen or has the same meaning as $R^1CO$, $R^4$ and $R^5$ independently of one another are alkyl groups containing 1 to 4 carbon atoms, m and n together stand for 0 or numbers of 1 to 12 and X stands for halide, alkyl sulfate or alkyl phosphate.

Finally, another group of suitable esterquats are the quaternized ester salts of fatty acids with 1,2-dihydroxypropyl dialkylamines corresponding to formula (III):

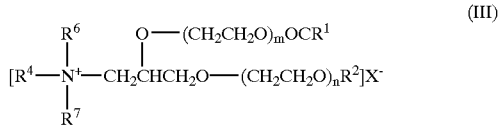

(III)

in which R¹CO is an acyl group containing 6 to 22 carbon atoms, R² is hydrogen or has the same meaning as R¹CO, R⁴, R⁶ and R⁷ independently of one another are alkyl groups containing 1 to 4 carbon atoms, m and n together stand for 0 or numbers of 1 to 12 and X stands for halide, alkyl sulfate or alkyl phosphate.

So far as the choice of the preferred fatty acids and the optimal degree of esterification are concerned, the examples mentioned for (I) also apply to the esterquats corresponding to formulae (II) and (III). The esterquats are normally marketed in the form of 50 to 90% by weight solutions in alcohol which may readily be diluted with water as required. The esterquats may also be used together with fatty alcohols in the form of flakes, as described, for example, in German patent DE-CL 4308794 (Henkel).

Aloe

Aloe—also known as atoin—is the thickened juice of leaves of aloe species (Liliaceae), mainly of Aloe vera (Curacao aloe) and Aloe ferox or Aloe africans (Cape aloe). Besides resins, the juice contains emodin, essential oils, above all about 5 to 25% by weight of the anthone derivative aloin. Other constituents are the pyrone derivative aloenin, various aloesaponols derived from anthracenone and the chromanone derivative aloesin. An overview of this subject can be found in PhiuZ, 13, 172 (1984).

Other Surfactants

The detergent mixtures according to the invention may contain other anionic, nonionic, cationic and/or amphoteric or zwifterionic surfactants in quantities of typically about 1 to 25% by weight and preferably 5 to 15% by weight, based on the detergent mixture. Typical examples of anionic surfactants are soaps, alkyl benzenesulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acyl amino acids such as, for example, acyl lactylates, acyl tartrates, acyl glutamates and acyl aspartates, alkyl oligoglucoside sulfates, protein fatty acid condensates (more particularly vegetable wheat-based products) and alkyl (ether)phosphates. Where the anionic surfactants contain polyglycol ether chains, they may have a conventional homolog distribution although they preferably have a narrow homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow homolog distribution. Typical examples of cationic surfactants are quaternary ammonium compounds, for example of the dimethyl distearyl ammonium chlorider type. Typical examples of amphoteric or zwitterionic surfactants are alkyl betaines, alkyl amidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralbladditive (Catalysts, Surfactants and Mineral Oil Additives)", Thieme Verlag, Stuttgart, 1978, pages 123–217.

Detergent Mixtures

In one preferred embodiment of the invention, the detergent mixtures are used in the form of aqueous preparations with a solids content of 15 to 70, preferably 25 to 50 and more particularly 35 to 45% by weight. The detergent mixtures preferably have the following composition:

(a) 1 to 50, preferably 5 to 40% by weight esterquats,
(b) 1 to 10, preferably 2 to 5% by weight aloe and
(c) 0 to 25, preferably 1 to 15% by weight other surfactants, with the proviso that the percentages add up to 100% by weight with water and optionally other auxiliaries and additives.

Commercial Applications

The detergent mixtures according to the invention have excellent cleaning performance and provide both synthetic and natural fibers with a pleasant soft feel. In addition, they reduce the electrostatic charging between the fibers and improve their rewettability. Accordingly, the present invention also relates to the use of the mixtures for the production of surface-active compositions such as, for example, laundry detergents, dishwashing detergents, cleaners and, in particular, softeners and cosmetic preparations such as, in particular, hair-care and body-care preparations.

Laundry and Dishwashing Detergents, Cleaners and Softeners

If the detergent mixtures according to the invention are used as laundry/dishwshing detergents, cleaners or softeners, they are normally present in liquid form. To produce powder-form detergents, the water-containing mixtures may be subsequently dried. Liquid preparations may have a non-aqueous component of 5 to 50 and preferably 15 to 35% by weight. In the most simple case, they are aqueous solutions of the mixtures mentioned. However, the liquid detergents may also be substantially water-free compositions. "Substantially water-free" in the context of this invention means that the composition preferably contains no free water which is not bound as water of crystallization or in a comparable form. In some cases, small quantities of free water—more particularly up to 5% by weight—are tolerable. The compositions used in the detergent field may contain other typical ingredients such as, for example, builders, bleaching agents, bleach activators, solvents, detergency boosters, enzymes, enzyme stabilizers, viscosity adjusters, redeposition inhibitors, optical brighteners, soil repellents, foam inhibitors, inorganic salts and dyes and perfumes.

Suitable liquid builders are ethylenediamine tetraacetic acid, nitrilotriacetic acid, citric acid and inorganic phosphonic acids such as, for example, the neutrally reacting sodium salts of 1-hydroxyethane-1,1-diphosphonate which may be present in quantities of 0.5 to 5 and preferably 1 to 2% by weight. A suitable solid builder is, in particular, finely crystalline zeolite containing synthetic and bound water, such as detergent-quality zeolite NaA. However, zeolite NaX and mixtures of NaA and NaX are also suitable. The zeolite may be used in the form of a spray-dried powder or even as an undried stabilized suspension still moist from its production. Where the zeolite is used in the form of a suspension, the suspension may contain small additions of nonionic surfactants as stabilizers, for example 1 to 3% by weight—based on zeolite—of ethoxylated $C_{12-18}$ fatty alcohols containing 2 to 5 ethylene oxide groups or ethoxylated isotridecanols. Suitable zeolites have a mean particle size of less than 10 $\mu$m (volume distribution, as measured by the Coulter Counter Method) and contain preferably 18 to 22% by weight and more preferably 20 to 22% by weight of bound water. Suitable substitutes or partial substitutes for zeolites are crystalline layer-form sodium silicates with the general formula NaMSi$_x$O$_{2x+1}$yH$_2$O, where M is sodium or hydrogen, x is a number of 1.9 to 4 and y is a number of 0 to 20, preferred values for x being 2, 3 or 4. Crystalline layer silicates such as these are described, for example, in European patent application EP 0 164 514 A. Preferred crystalline layer silicates are those in which M in the general formula stands for sodium and x assumes the value 2 or 3. Both β- and γ-sodium disilicates Na$_2$Si$_2$O$_5$yH$_2$O are particularly preferred, β-sodium disilicate being obtainable for example by the process described in International patent application WO 91/08171. The powder-form detergents according to the invention preferably contain 10 to 60% by weight of zeolite and/or crystalline layer silicates as solid builders, mixtures of zeolite and crystalline layer silicates in any ratio being particularly advantageous. In one particularly preferred embodiment, the detergents contain 20 to 50% by weight of zeolite and/or crystalline layer silicates. Particularly preferred detergents contain up to 40% by weight of zeolite and, more particularly, up to 35% by weight of zeolite, based on water-free active substance. Other suitable ingredients of the detergents are water-soluble amorphous silicates which are preferably used in combination with zeolite and/or crystalline layer silicates. Particularly preferred detergents are those which contain above all sodium silicate with a molar ratio of Na$_2$O to SiO$_2$ (modulus) of 1:1 to 1:4.5 and preferably 1:2 to 1:3.5. The amorphous sodium silicate content of the detergents is preferably up to 15% by weight and more preferably from 2 to 8% by weight. Phosphates, such as tripolyphosphates, pyrophosphates and orthophosphates, may also be present in the detergents in small quantities. The phosphate content of the detergents is preferably up to 15% by weight and, more particularly, from 0 to 10% by weight. In addition, the detergents may contain layer silicates of natural and synthetic origin. Corresponding layer silicates are known, for example, from patent applications DE 23 34 899 B, EP 0 026 529 A and DE 35 26 405 A. Their suitability for use is not confined to a particular composition or structural formula. However, smectites are preferred, bentonites being particularly preferred. Suitable layer silicates which belong to the group of water-swellable smectites are, for example, those corresponding to the following general formulae:

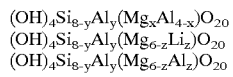

| | |
|---|---|
| (OH)$_4$Si$_{8-y}$Al$_y$(Mg$_x$Al$_{4-x}$)O$_{20}$ | montmorillonite |
| (OH)$_4$Si$_{8-y}$Al$_y$(Mg$_{6-z}$Li$_z$)O$_{20}$ | hectorite |
| (OH)$_4$Si$_{8-y}$Al$_y$(Mg$_{6-z}$Al$_z$)O$_{20}$ | saponite | where x=0 to 4, y=0 to 2 and z=0 to 6. In addition, small quantities of iron may be incorporated in the crystal lattice of the layer silicates corresponding to the above formulae.

By virtue of their ion-exchanging properties, the layer silicates may also contain hydrogen, alkali metal and alkaline earth metal ions, more particularly Na$^+$ and Ca$^{2+}$. The quantity of water of hydration is generally in the range from 8 to 20% by weight and is dependent upon the degree of swelling and upon the processing method. Suitable layer silicates are known, for example, from U.S. Pat. Nos. 3,966,629, 4,062,647, EP 0 026 529 A and EP 0 028 432 A. Layer silicates which have been substantially freed from calcium ions and strongly coloring iron ions by an alkali treatment are preferably used. Useful organic builders are, for example, the polycarboxylic acids preferably used in the form of their sodium salts, such as citric acid, adipic acidic acid, succinic acid, glutaric acid, tartaric acid, sugar acids, aminocarboxylic acids, nitrilotriacetic acid (NTA), providing their use is not ecologically unsafe, and mixtures thereof. Preferred salts are the salts of polycarboxylic acids, such as citric acid, adipic acid, succinic acid, glutaric acid, tartaric acid, sugar acids and mixtures thereof. Suitable polymeric polycarboxylates are, for example, the sodium salts of polyacrylic acid or polymethacrylic acid, for example those with a relative molecular weight of 800 to 150,000 (based on acid). Suitable copolymeric polycarboxylates are, in particular, those of acrylic acid with methacrylic acid and acrylic acid or methacrylic acid with maleic acid. Copolymers of acrylic acid with maleic acid which contain 50 to 90% by weight of acrylic acid and 50 to 10% by weight of maleic acid are particularly suitable. Their relative molecular weight, based on free acids, is generally in the range from 5,000 to 200,000, preferably in the range from 10,000 to 120,000 and more preferably in the range from 50,000 to 100,000. It is not absolutely essential to use polymeric polycarboxylates. However, if polymeric polycarboxylates are used, detergents containing biodegradable polymers, for example terpolymers which contain acrylic acid and maleic acid or salts thereof and vinyl alcohol or vinyl alcohol derivatives as monomers or acrylic acid and 2-alkyl allyl sulfonic acid or salts thereof and sugar derivatives as monomers are preferred. The terpolymers obtained in accordance with the teaching of German patent applications DE 42 21 381 A and DE 43 00 772 A are particularly preferred. Other suitable builders are polyacetals which may be obtained by reacting dialdehydes with polyol carboxylic acids containing 5 to 7 carbon atoms and at least 3 hydroxyl groups, for example as described in European patent application EP 0 280 223 A. Preferred polyacetals are obtained from dialdehydes, such as glyoxal, glutaraldehyde, terephthalaldehyde and mixtures thereof and from polyol carboxylic acids, such as gluconic acid and/or glucoheptonic acid.

Among the compounds yielding hydrogen peroxide in water which are used as bleaching agents, sodium perborate tetrahydrate and sodium perborate monohydrate are particularly important. Other suitable bleaching agents are, for example, peroxycarbonate, citrate perhydrates and salts of peracids, such as perbenzoates, peroxyphthalates or diperoxydodecanedioic acid. They are normally used in quantities of 8 to 25% by weight. Sodium perborate monohydrate is preferred and is used in quantities of 10 to 20% by weight and preferably in quantities of 10 to 15% by weight. By virtue of its ability to bind free water to form the tetrahydrate, it contributes towards increasing the stability of the detergent.

In order to obtain an improved bleaching effect where washing is carried out at temperatures of 60° C. or lower, bleach activators may be incorporated in the preparations. Examples of bleach activators are N-acyl and O-acyl compounds which form organic peracids with hydrogen peroxide, preferably N,N'-tetraacylated diamines, also carboxylic anhydrides and esters of polyols, such as glucose pentaacetate. The bleach activator content of bleach-containing detergents is in the usual range, i.e. preferably between 1 and 10% by weight and more preferably between 3 and 8% by weight. Particularly preferred bleach activators are N,N,N',N'-tetraacetyl ethylenediamine and 1,5-diacetyl-2,4-dioxohexahydro-1,3,5-triazine.

Suitable organic solvents are, for example, monohydric and/or polyhydric alcohols containing 1 to 6 carbon atoms and preferably 1 to 4 carbon atoms. Preferred alcohols are ethanol, propane-1,2-diol, glycerol and mixtures thereof. The detergents preferably contain 2 to 20% by weight and more preferably 5 to 15% by weight of ethanol or a mixture of ethanol and propane-1,2-diol or, more particularly, of ethanol and glycerol. In another possible embodiment, the preparations contain polyethylene glycol with a relative molecular weight of 200 to 2,000 and preferably up to 600 in quantities of 2 to 17% by weight either in addition to the monohydric and/or polyhydric alcohols containing 1 to 6 carbon atoms or on its own. Suitable hydrotropes are, for example, toluene sulfonate, xylene sulfonate, cumene sulfonate or mixtures thereof.

Suitable enzymes are those from the class of proteases, lipases, amylases, cellulases and mixtures thereof. Enzymes obtained from bacterial strains or fungi, such as *Bacillus subtilis, Bacillus licheniformis* and *Streptomyces griseus,* are particularly suitable. Proteases of the subtilisin type are preferably used, proteases obtained from *Bacillus lentus* being particularly preferred. They may be used in quantities of about 0.2 to about 2% by weight. The enzymes may be adsorbed onto supports and/or embedded in shell-forming materials to protect them against premature decomposition. In addition to the monohydric and polyhydric alcohols and the phosphonates, the detergents may contain other enzyme stabilizers. For example, 0.5 to 1% by weight of sodium formate may be used. It is also possible to use proteases which are stabilized with soluble calcium salts and which have a calcium content of preferably about 1.2% by weight, based on the enzyme. However, it is of particular advantage to use boron compounds, for example boric acid, boron oxide, borax and other alkali metal borates, such as the salts of orthoboric acid ($H_3BO_3$), metaboric acid ($HBO_2$) and pyroboric acid (tetraboric acid $H_2B_4O_7$).

Suitable viscosity adjusters are, for example, hydrogenated castor oil, salts of long-chain fatty acids, which are preferably used in quantities of 0 to 5% by weight and more preferably in quantities of 0.5 to 2% by weight, for example sodium, potassium, aluminium, magnesium and titanium stearates or the sodium and/or potassium salts of behenic acid, and other polymeric compounds. Preferred other polymeric compounds include polyvinyl pyrrolidone, urethanes and the salts of polymeric polycarboxylates, for example homopolymeric or copolymeric polyacrylates, polymethacrylates and, in particular, copolymers of acrylic acid with maleic acid, preferably those of 50% to 10% maleic acid. The relative molecular weight of the homopolymers is generally between 1,000 and 100,000 while the relative molecular weight of the copolymers is between 2,000 and 200,000 and preferably between 50,000 and 120,000, based on the free acid. Water-soluble polyacrylates which are crosslinked, for example, with about 1% of a polyallyl ether of sucrose and which have a relative molecular weight above 1,000,000 are also particularly suitable. Examples include the polymers with a thickening effect obtainable under the name of Carbopol® 940 and 941. The crosslinked polyacrylates are preferably used in quantities of not more than 1% by weight and more preferably in quantities of 0.2 to 0.7% by weight. The detergents may additionally contain about 5 to 20% by weight of a partly esterified copolymer of the type described in European patent application EP 0 367 049 A. These partly esterified polymers are obtained by copolymerization of (a) at least one $C_{4-28}$ olefin or mixtures of at least one $C_{4-28}$ olefin with up to 20 mole-% of $C_{1-28}$ alkyl vinyl ethers and (b) ethylenically unsaturated dicarboxylic anhydrides containing 4 to 8 carbon atoms in a molar ratio of 1:1 to form copolymers with K values of 6 to 100 and subsequent partial esterification of the copolymers with reaction products, such as $C_{1-13}$ alcohols, $C_{8-22}$ fatty acids, $C_{1-12}$ alkyl phenols, secondary $C_{2-30}$ amines or mixtures thereof, with at least one $C_{2-4}$ alkylene oxide or tetrahydrofuran and hydrolysis of the anhydride groups of the copolymers to carboxyl groups, the partial esterification of the copolymers being continued to such an extent that 5 to 50% of the carboxyl groups of the copolymers are esterified. Preferred copolymers contain maleic anhydride as the ethylenically unsaturated dicarboxylic anhydride. The partly esterified copolymers may be present either in the form of the free acid or preferably in partly or completely neutralized form. The copolymers are advantageously used in the form of an aqueous solution, more particularly in the form of a 40 to 50% by weight solution. The copolymers not only contribute towards the single wash cycle and multiple wash cycle performance of the liquid detergent, they also promote a desirable reduction in viscosity of the concentrated liquid detergents. By using these partly esterified copolymers, it is possible to obtain concentrated aqueous liquid detergents which flow under the sole effect of gravity, i.e. without any need for other shear forces. In a preferred embodiment, the concentrated aqueous liquid detergents contain partly esterified copolymers in quantities of 5 to 15% by weight and, more particularly, in quantities of 8 to 12% by weight.

The function of redeposition inhibitors is to keep the soil detached from the fibers suspended in the wash liquor and thus to prevent discoloration. Suitable redeposition inhibitors are water-soluble, generally organic colloids, for example the water-soluble salts of polymeric carboxylic acids, glue, gelatin, salts of ether carboxylic acids or ether sulfonic acids of starch or cellulose or salts of acidic sulfuric acid esters of cellulose or starch. Water-soluble polyamides containing acidic groups are also suitable for this purpose. Soluble starch preparations and other starch products than those mentioned above, for example degraded starch, aldehyde starches, etc., may also be used. Polyvinyl pyrrolidone is also suitable. However, cellulose ethers, such as carboxymethyl cellulose, methyl cellulose, hydroxyalkyl cellulose, and mixed ethers, such as methyl hydroxyethyl cellulose, methyl hydroxypropyl cellulose, methyl carboxymethyl cellulose and mixtures thereof, and polyvinyl pyrrolidone are preferably used, for example in quantities of 0.1 to 5% by weight, based on the detergent.

The detergents may contain derivatives of diaminostilbene disulfonic acid or alkali metal salts thereof as optical brighteners. Suitable optical brighteners are, for example, salts of 4,4'-bis-(2-anilino-4-morpholino-1,3,5-triazinyl-6-amino)stilbene-2,2'-disulfonic acid or compounds of similar structure which, instead of the morpholino group, contain a diethanolamino group, a methylamino group, an anilino group or a 2-methoxyethylamino group. Brighteners of the substituted diphenyl styryl type, for example alkali metal salts of 4,4'-bis-(2-sulfostyryl)-diphenyl, 4,4'-bis-(4-chloro-3-sulfostyryl)-diphenyl or 4-(4-chlorostyryl)4'-(2-sulfostyryl)-diphenyl, may also be present. Mixtures of the brighteners mentioned above may also be used. Uniformly white granules are obtained if, in addition to the usual brighteners in the usual quantities, for example between 0.1 and 0.5% by weight and preferably between 0.1 and 0.3% by weight, the detergents also contain small quantities, for example $10^{-6}$ to $10^{-3}$% by weight and preferably around $10^{-5}$% by weight, of a blue dye. A particularly preferred dye is Tinolux® (a product of Ciba-Geigy).

Suitable soil repellents are substances which preferably contain ethylene terephthalate and/or polyethylene glycol terephthalate groups, the molar ratio of ethylene terephthalate to polyethylene glycol terephthalate being in the range from 50:50 to 90:10. The molecular weight of the linking polyethylene glycol units is more particularly in the range from 750 to 5,000, i.e. the degree of ethoxylation of the polymers containing polyethylene glycol groups may be about 15 to 100. The polymers are distinguished by an average molecular weight of about 5,000 to 200,000 and may have a block structure, but preferably have a random structure. Preferred polymers are those with molar ethylene terephthalate: polyethylene glycol terephthalate ratios of about 65:35 to about 90:10 and preferably in the range from about 70:30 to 80:20. Other preferred polymers are those which contain linking polyethylene glycol units with a molecular weight of 750 to 5,000 and preferably in the range from 1,000 to about 3,000 and which have a molecular weight of the polymer of about 10,000 to about 50,000. Examples of commercially available polymers are the products Milease® T (ICI) or Repelotex® SRP 3 (Rhône-Poulenc).

Where the detergents are used in washing machines, it can be of advantage to add conventional foam inhibitors to them. Suitable foam inhibitors are, for example, soaps of natural or synthetic origin which have a high percentage of $C_{18-24}$ fatty acids. Suitable non-surface-active foam inhibitors are, for example, organopolysiloxanes and mixtures thereof with microfine, optionally silanized silica and paraffins, waxes, microcrystalline waxes and mixtures thereof with silanized silica of bis-stearyl ethylenediamide. Mixtures of various foam inhibitors, for example mixtures of silicones, paraffins or waxes, may also be used with advantage. The foam inhibitors, more particularly silicone- or paraffin-containing foam inhibitors, are preferably fixed to a granular water-soluble or water-dispersible carrier/support. Mixtures of paraffins and bis-stearyl ethylenediamides are particularly preferred.

The pH value of liquid detergents, more especially concentrated liquid detergents, is generally in the range from 7 to 10.5, preferably in the range from 7 to 9.5 and more preferably in the range from 7 to 8.5. Higher pH values, for example above 9, can be adjusted by using small quantities of sodium hydroxide or alkaline salts, such as sodium carbonate or sodium silicate. The liquid preparations generally have viscosities of 150 to 10,000 mPas (Brookfield viscosimeter, spindle 1, 20 r.p.m., 20° C.). The substantially water-free detergents preferably have viscosities of 150 to 5,000 mPas. The viscosity of aqueous detergents is preferably below 2,000 mPas and, more particularly, in the range from 150 to 1,000 mPas.

Production of Solid Compositions

The bulk density of the solid compositions is generally in the range from 300 to 1,200 g/l and more particularly in the range from 500 to 1,100 g/l. They may be produced by any of the known methods, such as mixing, spray drying, granulation and extrusion. Processes in which several components, for example spray-dried components and granulated and/or extruded components, are mixed with one another are particularly suitable. The spray-dried or granulated components may also be subsequently treated, for example with nonionic surfactants, more particularly ethoxylated fatty alcohols, by any of the usual methods. In granulation and extrusion processes in particular, any anionic surfactants present are preferably used in the form of a spray-dried, granulated or extruded compound either as an added component in the process or as an additive to other granules. The preferred relatively heavy granules with bulk densities above 600 g/l in particular preferably contain components which improve the dispensing behavior and/or the dissolving behavior of the granules. Alkoxylated fatty alcohols containing 12 to 80 moles of ethylene oxide per mole of alcohol, for example tallow fatty alcohol containing 14 EO, 30 EO or 40 EO, and polyethylene glycols with a relative molecular weight of 200 to 12,000 and preferably in the range from 200 to 600, are advantageously used for this purpose.

It is also possible and, depending on the formulation, can be of advantage subsequently to add other individual ingredients of the detergent, for example citrate or citric acid or other polycarboxylates or polycarboxylic acids, polymeric polycarboxylates, zeolite and/or layer silicates, which may optionally be crystalline, to spray-dried, granulated and/or extruded components optionally treated with nonionic surfactants and/or other ingredients which are liquid to wax-like at the processing temperature. A preferred process in this regard is one in which the surface of ingredients of the detergent or the detergent as a whole is subsequently treated to reduce the tackiness of the granules rich in nonionic surfactants and/or to improve their solubility. Suitable surface modifiers are known from the prior art. Besides other suitable surface modifiers, fine-particle zeolites, silicas, amorphous silicates, fatty acids or fatty acid salts, for example calcium stearate, but especially mixtures of zeolite and silicas or zeolite and calcium stearate, are particularly preferred.

Cosmetic and/or Pharmaceutical Preparations

The detergent mixtures according to the invention may also be used for the production of cosmetic and/or pharmaceutical preparations, for example hair shampoos, hair lotions, foam baths, shower baths, creams, gels, lotions, alcoholic and aqueous/alcoholic solutions, emulsions, wax/fat compounds, stick preparations, powders or ointments. These preparations may also contain oil components, emulsifiers, superfatting agents, pearlizing waxes, consistency promoters, thickeners, polymers, silicone compounds, fats, waxes, stabilizers, biogenic agents, deodorizers, anti-dandruff agents, film formers, swelling agents, UV protection factors, antioxidants, hydrotropes, preservatives, insect repellents, self-tanning agents, solubilizers, perfume oils, dyes, germ inhibitors and the like as further auxiliaries and additives.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example squalane and squalene.

Suitable emulsifiers are, for example, nonionic surfactants from at least one of the following groups:

(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and to alkylphenols containing 8 to 15 carbon atoms in the alkyl group;

(2) $C_{12/18}$ fatty acid monoesters and diesters of products of the addition of 1 to 30 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) adducts of 15 to 60 moles of ethylene oxide with castor oil and/or hydrogenated castor oil;

(6) polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

(7) products of the addition of 2 to 15 moles of ethylene oxide onto castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) mono-, di and trialkyl phosphates and mono-, di- and/or tri-PEG-alkyl phosphates and salts thereof;

(10) wool wax alcohols;

(11) polysiloxane/polyalkyl polyether copolymers and corresponding derivatives;

(12) mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol,

(13) polyalkylene glycols and

(14) glycerol carbonate.

The addition products of ethylene oxide and/or propylene oxide with fatty alcohols, fatty acids, alkylphenols, glycerol mono- and diesters and sorbitan mono- and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE 2024051 PS.

$C_{8/18}$ alkyl mono- and oligoglycosides, their production and their use as surfactants are known from the prior art. They are produced in particular by reaction of glucose or oligosaccharides with primary alcohols containing 8 to 18 C atoms. So far as the glycoside component is concerned, both monoglycosides, in which a cyclic sugar unit is attached to the fatty alcohol by a glycoside linkage, and oligomeric glycosides with a degree of oligomerization of preferably up to about 8 are suitable. The degree of oligomerization is a statistical mean value on which a homolog distribution typical of such technical products is based.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, preferably methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Typical examples of fats are glycerides while suitable waxes are inter alia beeswax, carnauba wax, candelilla wax, montan wax, paraffin wax, hydrogenated castor oils, fatty acid esters solid at room temperature or microwaxes, optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizers are, for example, antiperspirants, such as aluminium chlorhydrates. These antiperspirants are colorless hygroscopic crystals which readily deliquesce in air and which accumulate when aqueous aluminium chloride solutions are concentrated by evaporation. Aluminium chlorhydrate is used for the production of perspiration-inhibiting and deodorizing compositions and probably acts by partially blocking the sweat glands through the precipitation of proteins and/or polysaccharides [cf. J. Soc. Cosm. Chem. 24, 281 (1973)]. For example, an aluminium chlorhydrate which corresponds to the formula $[Al_2(OH)_5Cl].2.5H_2O$ and which is particularly preferred for the purposes of the invention is commercially available under the name of Locron® from Hoechst AG of Frankfurt, FRG [cf. J. Pharm. Pharmcol. 26, 531 (1975)]. Besides the chlorhydrates, aluminium hydroxylactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGaA, Dusseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective.

Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor, as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone, as described in EP 0 818 450 A1;

propane-1,3-diones such as, for example, 1-(4-tert.butylphenyl)-3-(4'-methoxyphenyl)-propane-1,3-dione;

ketotricyclo(5.2.1)decane derivatives, as described in EP 0 694 521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert-butyl-4'-methoxydibenzoylmethane (Parsol 1789) or 1-phenyl-3-(4'-isopropylphenyl)-propane-1,3dione. The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof.

Silicates (talcum), barium sulfate and zinc stearate may be used as salts. The oxides and salts are used in the form of the pigments for skin-care and skin-protecting emulsions and decorative cosmetics. The particles should have an average diameter of less than 100 nm, preferably from 5 to 50 nm and more preferably from 15 to 30 nm. They may be spherical in shape although ellipsoidal particles or other nonspherical particles may also be used. The pigments may also be surface-treated,. i.e. hydrophilicized or hydrophobicized. Typical examples are coated titanium dioxides such as, for example, Ttitandioxid T 805 (Degussa) or Eusolex® T2000 (Merck). Suitable hydrophobic coating materials are, above all, silicones and especially trialkoxyoctyl silanes or simethicones. So-called micro- or nanopigments are preferably used in sun protection products. Micronized zinc oxide is preferably used. Other suitable UV filters can be found in P. Finkel's review in SÖFW-Journal 122, 543 (1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-camosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to $\mu$mole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, camosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes such as, for example, ethanol, isopropyl alcohol or polyols may be used to improve flow behavior. Suitable polyols preferably contain 2 to 15 carbon atoms and at least two hydroxyl groups. The polyols may contain other functional groups, especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose;

aminosugars such as, for example, glucamine;

dialcoholamines, such as diethanolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenylbiguanido)-hexane) or TCC (3,4,4'-trichlorocarbanilide). Numerous perfumes and essential oils also have antimicrobial properties. Typical examples are the active substances eugenol, menthol and thymol in clove, mint and thyme oil. An interesting natural deodorant is the terpene alcohol farnesol (3,7,11-trimethyl-2,6,10-dodecatrien-1-ol) which is present in linden blossom oil and which smells of lily-of-the-valley. Glycerol monolaurate has also been successfully used as a bacteriostatic agent. The percentage content of the additional germ-inhibiting agents is normally about 0.1 to 2% by weight, based on the solids component of the preparations.

The total percentage content of auxiliaries and additives may be from 1 to 50% by weight and is preferably from 5 to 40% by weight, based on the particular composition. The preparations may be produced by standard hot or cold processes and are preferably produced by the phase inversion temperature method.

EXAMPLES

The dermatological compatibility of the detergent mixtures was determined by OECD Method No. 404 and EEC Directive 84/449 EEC, Pt. B.4. The total irritation scores shown were formed from the irritation scores obtained after 24, 48 and 72 h. The total irritation score determined in comparison test C1 was put at 100% and the scores obtained in the other tests were related to that score. Softness was evaluated by a panel of 6 trained examiners who assessed the washed cotton fabric on a scale of (1)=very soft to (4)=hard. Hydrophilia, i.e. the rewettability of the fabric, was determined by the known height-of-rise test to DIN 53924 in which 1 cm wide strips of the cotton fabric are immersed in water and the height to which the water rises in the fabric in 1 minute under the effect of the capillary forces is measured. The greater the height of rise, the higher the hydrophilia of the fabric. Wet combability was measured on brown hair (Alkinco #6634, tress length 12 cm, tress weight 1 g). After the zero measurement, the tresses were soaked with 1000 ml of the formulations. After soaking for 5 minutes, the tresses were rinsed out for 1 minute under running water (1 l/min., 38° C.). The tresses were remeasured and compared with the zero measurement. The measurement error was on average 2% and the statistical certainty 99%. The results are set out in Tables 1 and 2. Examples 1 to 14 correspond to the invention, Examples C1 and C2 are intended for comparison.

TABLE 1

Composition and performance of detergent mixtures

| Composition/performance | 1 | 2 | 3 | 4 | 5 | 6 | 7 | 8 | C1 | C2 |
|---|---|---|---|---|---|---|---|---|---|---|
| Esterquat* | 35.0 | 35.0 | 30.0 | 30.0 | 30.0 | 30.0 | 30.0 | 30.0 | — | — |
| Distearyl dimethylammonium chloride | — | — | — | — | — | — | — | — | 35.0 | 35.0 |
| Aloe vera | 1.0 | — | 1.0 | 1.0 | 1.0 | — | — | — | — | 1.0 |
| Aloe ferox | — | 1.0 | — | — | — | 1.0 | 1.0 | 1.0 | — | — |
| Coco Glucosides | — | — | 5.0 | — | 3.0 | 5.0 | — | 3.0 | — | — |
| Cocamidopropyl Betaine | — | — | — | 5.0 | 2.0 | — | 5.0 | 2.0 | — | — |
| Water | | | | | to 100 | | | | | |
| Total irritation score [%-rel] | 84 | 85 | 80 | 76 | 72 | 80 | 77 | 72 | 100 | 90 |
| Softness | 1.5 | 1.5 | 1.5 | 1.5 | 1.5 | 1.5 | 1.5 | 1.5 | 2.5 | 2.5 |
| Hydrophilia [mm] | 11 | 12 | 12 | 12 | 11 | 12 | 11 | 12 | 8 | 9 |
| Wet combability [mV] | 44.3 | 45.1 | 47.2 | 46.8 | 48.1 | 47.5 | 46.5 | 47.1 | 36.1 | 37.0 |

*) Methyl-quaternized ditallow fatty acid triethanolamine ester, methyl sulfate salt (Dehyquart Au 46, Henkel KGaA, Düsseldorf)

TABLE 2

Composition and performance of detergent mixtures

| Composition/performance | 9 | 10 | 11 | 12 | 13 | 14 |
|---|---|---|---|---|---|---|
| Esterquat 1 | 35.0 | — | — | — | — | — |
| Esterquat 2 | — | 35.0 | — | — | — | — |
| Esterquat 3 | — | — | 35.0 | — | — | — |
| Esterquat 4 | — | — | — | 35.0 | — | — |
| Esterquat 5 | — | — | — | — | 35.0 | — |
| Esterquat 6 | — | — | — | — | — | 35.0 |
| Aloe vera | 1.0 | 1.0 | 1.0 | 1.0 | 1.0 | 1.0 |
| Water | | | to 100 | | | |
| Total irritation score [%-rel] | 85 | 83 | 84 | 85 | 82 | 83 |
| Softness | 1.5 | 2.0 | 2.0 | 2.0 | 2.0 | 2.0 |
| Hydrophilia [mm] | 11 | 10 | 10 | 10 | 10 | 10 |
| Wet combability [mV] | 44.0 | 45.0 | 40.0 | 49.1 | 46.1 | 45.6 |

(1) Dipalmitoylethyl Hydroxyethylmonium Methosulfate (Dehyquart AU 56)
(2) Dipalmitoylethyl Hydroxyethylmonium Methosulfate (and) Cetearyl Alcohol (and) Ceteareth-20 (Dehyquart C 4043)
(3) Dipalmitoyl/adipinolethyl Hydroxyethylmonium Methosulfate (Dehyquart D 6003)
(4) Dipalmitoylethyl Hydroxyethylmonium Methosulfate (and) Ceteryll Alcohol (Dehyquart F 75)
(5) Dipalmitoylethyl Hydroxyethylmonium Methosulfate (and) Cocoglycerides (and) Glycerin (Dehyquart F 100)
(6) Dicocoylethyl Hydroxyethylmonium Methosulfate (and) Propylene Glycol (Dehyquart L 80) - all Henkel KGaA, Düsseldorf

TABLE 3

Cosmetic preparations (water, preservative to 100% by weight)

| Composition (INCI) | 1 | 2 | 3 | 4 | 5 | 6 | 7 | 8 | 9 | 10 |
|---|---|---|---|---|---|---|---|---|---|---|
| Texapon ® NSO<br>Sodium Laureth Sulfate | — | — | — | — | — | — | 38.0 | 38.0 | 25.0 | — |
| Texapon ® SB 3<br>Disodium Laureth Sulfosuccinate | — | — | — | — | — | — | — | — | 10.0 | — |
| Plantacare ® 818<br>Coco Glucosides | 2.0 | — | — | — | — | — | 7.0 | 7.0 | 6.0 | — |
| Plantacare ® PS 10<br>Sodium Laureth Sulfate (and) Coco Glucosides | — | — | — | — | — | — | — | — | — | 16.0 |
| Dehyton ® PK 45<br>Cocamidopropyl Betaine | — | — | — | — | — | — | — | — | 10.0 | — |
| Dehyquart ® F 75<br>Dipalmitoylethyl Hydroxyethylmonium Methosulfate (and) Cetearyl Alcohol (and) Ceteareth-20 | 1.0 | 1.0 | 1.0 | 1.0 | 1.0 | 1.0 | 1.0 | 1.0 | 1.0 | 1.0 |
| Emulgade ® PL 68/50<br>Cetearyl Glucoside (and) Cetearyl Alcohol | 4.0 | — | — | — | — | — | — | — | — | — |
| Eumulgin ® B2<br>Ceteareth-20 | — | 0.8 | — | 0.8 | — | 1.0 | — | — | — | — |
| Eumulgin ® VL 75<br>Lauryl Glucoside (and) Polyglyceryl-2 Polyhydroxystearate (and) Glycerin | — | — | 0.8 | — | 0.8 | — | — | — | — | — |

TABLE 3-continued

| Cosmetic preparations (water, preservative to 100% by weight) | | | | | | | | | | |
|---|---|---|---|---|---|---|---|---|---|---|
| Lanette ® O<br>Cetearyl Alcohol | — | 2.5 | 2.5 | 2.5 | 3.0 | 2.5 | — | — | — | — |
| Lameform ® TGI<br>Polyglyceryl-3 Isostearate | 1.0 | — | — | 1.0 | — | — | — | — | — | — |
| Dehymuls ® PGPH<br>Polyglyceryl-2 Dipolyhydroxystearate | — | — | — | — | 1.0 | — | — | — | — | — |
| Cutina ® GMS<br>Glyceryl Stearate | 0.5 | 0.5 | 0.5 | 0.5 | 0.5 | 1.0 | — | — | — | — |
| Cetiol ® HE<br>PEG-7 Glyceryl Cocoate | — | — | — | — | — | — | — | — | 1.0 | — |
| Cetiol ® OE<br>Dicaprylyl Ether | — | 1.0 | — | — | — | — | — | — | — | — |
| Cetiol ® PGL<br>Hexyldecanol (and) Hexyldecyl laurate | — | — | — | — | 1.0 | — | — | — | — | — |
| Cetiol ® V<br>Decyl Oleate | 1.0 | — | — | 1.0 | — | — | — | — | — | — |
| Eutanol ® G<br>Octyldodecanol | — | — | 1.0 | — | — | 1.0 | — | — | — | — |
| Nutrilan ® Keratin W<br>Hydrolyzed Keratin | 2.3 | — | — | — | — | — | — | — | — | — |
| Nutrilan ® I<br>Hydrolyzed Collagen | — | — | — | 2.0 | — | — | — | — | — | — |
| Lamesoft ® LMG<br>Glyceryl Laurate (and) Potassium Cocoyl Hydrolyzed Collagen | — | — | — | — | — | — | 3.0 | 2.0 | 4.0 | — |
| Gluadin ® WK<br>Sodium Cocoyl Hydrolyzed Wheat Protein | 1.0 | 1.0 | 1.0 | 1.0 | 1.0 | 1.5 | 0.5 | 0.5 | 0.5 | 0.5 |
| Euperlan ® PK 3000 AM<br>Glycol Distearate (and) Laureth-4 (and) Cocamidopropyl Betaine | — | — | — | — | — | — | — | 3.0 | 5.0 | 5.0 |
| Generol ® 122 N<br>Soja Sterol | — | — | — | — | 1.0 | 1.0 | — | — | — | — |
| Aloe Vera Gel Concentrate<br>Aloe Barbadensis (and) Citric Acid (and) Ascorbic Acid | 1.0 | 1.0 | 1.0 | 1.0 | 1.0 | 1.0 | 1.0 | 1.0 | 1.0 | 1.0 |
| Arylpon ® F<br>Laureth-2 | | | | | | | 3.0 | 3.0 | 1.0 | |
| Sodium Chloride | — | — | — | — | — | — | — | 1.5 | | 1.5 |

| Composition (INCI) | 11 | 12 | 13 | 14 | 15 | 16 | 17 | 18 | 19 | 20 |
|---|---|---|---|---|---|---|---|---|---|---|
| Texapon ® NSO<br>Sodium Laureth Sulfate | 20.0 | 20.0 | 12.4 | — | 25.0 | 11.0 | — | — | — | — |
| Texpon ® K 14 S<br>Sodium Myreth Sulfate | — | — | — | — | — | — | — | — | 11.0 | 23.0 |
| Texapon ® SB 3<br>Disodium Laureth Sulfosuccinate | — | — | — | — | — | 7.0 | — | — | — | — |
| Plantacare ® 818<br>Coco Glucosides | 5.0 | 5.0 | 4.0 | — | — | — | — | — | 6.0 | 4.0 |
| Plantacare ® 2000<br>Decyl Glucoside | — | — | — | — | 5.0 | 4.0 | — | — | — | — |
| Plantacare ® PS 10<br>Sodium Laureth Sulfate (and) Coco Glucosides | — | — | — | 40.0 | — | — | 16.0 | 17.0 | — | — |
| Dehyton ® PK 45<br>Cocamidopropyl Betaine | 20.0 | 20.0 | — | — | 8.0 | — | — | — | — | 7.0 |
| Dehyquart ® F 75<br>Dipalmitoylethyl Hydroxyethylmonium Methosulfate (and) Cetearyl Alcohol (and) Ceteareth-20 | 1.0 | 1.0 | 1.0 | 1.0 | 1.0 | 1.0 | 1.0 | 1.0 | 1.0 | 1.0 |
| Eumulgin ® B1<br>Ceteareth-12 | — | — | — | — | 1.0 | — | — | — | — | — |
| Eumulgin ® B2<br>Ceteareth-20 | — | — | — | 1.0 | — | — | — | — | — | — |
| Lameform ® TGI<br>Polyglyceryl-3 Isostearate | — | — | — | 4.0 | — | — | — | — | — | — |
| Dehymuls ® PGPH<br>Polyglyceryl-2 Dipolyhydroxystearate | — | — | 1.0 | — | — | — | — | — | — | — |
| Monomuls ® 90-L 12<br>Glyceryl Laurate | — | — | — | — | — | — | — | — | — | 1.0 |
| Cutina ® GMS<br>Glyceryl Stearate | — | — | — | — | — | — | — | — | 1.0 | — |
| Cetiol ® HE<br>PEG-7 Glyceryl Cocoate | — | 0.2 | — | — | — | — | — | — | — | — |
| Eutanol ® G<br>Octyldodecanol | — | — | — | 3.0 | — | — | — | — | — | — |
| Nutrilan ® Keratin W<br>Hydrolyzed Keratin | — | — | — | — | — | — | — | — | 2.0 | 2.0 |
| Nutrilan ® I | 1.0 | — | — | — | — | 2.0 | — | 2.0 | — | — |

TABLE 3-continued

Cosmetic preparations (water, preservative to 100% by weight)

| Composition (INCI) | | | | | | | | | | |
|---|---|---|---|---|---|---|---|---|---|---|
| Hydrolyzed Collagen | | | | | | | | | | |
| Lamesoft ® LMG<br>Glyceryl Laurate (and) Potassium Cocoyl Hydrolyzed Collagen | — | — | — | — | — | — | — | — | 1.0 | — |
| Lamesoft ® 156<br>Hydrogenated Tallow Glyceride (and) Potassium Cocoyl Hydrolyzed Collagen | — | — | — | — | — | — | — | — | — | 5.0 |
| Gluadin ® WK<br>Sodium Cocoyl Hydrolyzed Wheat Protein | 1.0 | 1.5 | 4.0 | 1.0 | 3.0 | 1.0 | 2.0 | 2.0 | 2.0 | — |
| Euperlan ® PK 3000 AM<br>Glycol Distearate (and) Laureth-4 (and) Cocamidopropyl Betaine | 5.0 | 3.0 | 4.0 | — | — | — | — | 3.0 | 3.0 | — |
| Aloe Vera Gel Concentrate<br>Aloe Barbadensis (and) Citric Acid (and) Ascorbic Acid | 1.0 | 1.0 | 1.0 | 1.0 | 1.0 | 1.0 | 1.0 | 1.0 | 1.0 | 1.0 |
| Arylpon ® F<br>Laureth-2 | 2.6 | 1.6 | — | 1.0 | 1.5 | — | — | — | — | — |
| Sodium Chloride | — | — | — | — | — | 1.6 | 2.0 | 2.2 | — | 3.0 |
| Glycerin (86% by weight) | — | 5.0 | — | — | — | — | — | 1.0 | 3.0 | — |

| Composition (INCI) | 21 | 22 | 23 | 24 | 25 | 26 | 27 | 28 | 29 | 30 |
|---|---|---|---|---|---|---|---|---|---|---|
| Texapon ® NSO<br>Sodium Laureth Sulfate | — | 30.0 | — | — | 25.0 | — | — | — | — | — |
| Plantacare ® 818<br>Coco Glucosides | — | 10.0 | 30.0 | — | 20.0 | — | — | — | — | — |
| Plantacare ® PS 10<br>Sodium Laureth Sulfate (and) Coco Glucosides | 22.0 | — | — | 22.0 | — | — | — | — | — | — |
| Dehyton ® PK 45<br>Cocamidopropyl Betaine | 15.0 | 10.0 | 100 | 15.0 | 20.0 | — | — | — | — | — |
| Dehyquart ® F 100<br>Dipalmitoylethyl Hydroxyethylmonium Methosulfate (and) Cocoglycerides | 2.0 | 2.0 | 2.0 | 2.0 | 2.0 | 2.0 | 2.0 | 2.0 | 2.0 | 2.0 |
| Emulgade ® SE<br>Glyceryl Stearate (and) Ceteareth 12/20 (and) Cetearyl Alcohol (and) Cetyl Palmitate | — | — | 15.0 | — | — | 5.0 | 5.0 | 6.0 | — | — |
| Eumulgin ® HRE 60<br>PEG 60 Hydrogenated Castor Oil | — | — | — | — | 5.0 | — | — | — | — | — |
| Lameform ® TGI<br>Polyglyceryl-3 Isostearate | — | — | — | — | — | — | — | — | 4.0 | — |
| Dehymuls ® PGPH<br>Polyglyceryl-2 Dipolyhydroxystearate | — | — | 3.8 | — | — | — | — | — | — | — |
| Monomuls ® 90-O 18<br>Glyceryl Oleate | — | — | — | — | — | — | — | — | 2.0 | — |
| Cetiol ® HE<br>PEG-7 Glyceryl Cocoate | 2.0 | — | — | 2.0 | 5.0 | — | — | — | — | 2.0 |
| Cetiol ® OE<br>Dicaprylyl Ether | — | — | — | — | — | — | — | 3.0 | 5.0 | 5.0 |
| Cetiol ® PGL<br>Hexyldecanol (and) Hexyldecyl Laurate | — | — | — | — | — | — | — | 3.0 | 10.0 | — |
| Cetiol ® SN<br>Cetearyl Isononanoate | — | — | — | — | — | 3.0 | 3.0 | — | — | 10.0 |
| Cetiol ® V<br>Decyl Oleate | — | — | — | — | — | 3.0 | 3.0 | — | — | — |
| Myritol ® 318<br>Coco Caprylate Caprate | — | — | — | — | — | — | — | — | 5.0 | 5.0 |
| Melissa oil | — | — | 5.0 | — | — | — | — | — | — | — |
| Bees Wax | — | — | — | — | — | — | — | — | 7.0 | 7.0 |
| Nutrilan ® Keratin W<br>Hydrolyzed Keratin | — | — | — | — | — | 40.0 | 60.0 | 60.0 | — | — |
| Nutrilan ® I<br>Hydrolyzed Collagen | — | — | — | — | 2.0 | — | — | — | — | — |
| Lamesoft ® LMG<br>Glyceryl Laurate (and) Potassium Cocoyl Hydrolyzed Collagen | — | 4.0 | — | — | — | — | — | — | — | — |
| Gluadin ® AGP<br>Hydolyzed Wheat Gluten | 0.5 | 0.5 | — | — | — | — | — | — | — | — |
| Gluadin ® WK<br>Sodium Cocoyl Hydrolyzed Wheat Protein | 2.0 | 2.0 | 4.0 | 2.0 | 5.0 | — | — | — | 5.0 | 5.0 |
| Euperlan ® PK 3000 AM<br>Glycol Distearate (and) Laureth-4 (and) Cocamidopropyl Betaine | 5.0 | — | — | 5.0 | — | — | — | — | — | — |
| Aloe Vera Gel Concentrate<br>Aloe Barbadensis (and) Citric Acid (and) Ascorbic Acid | 1.0 | 1.0 | 1.0 | 1.0 | 1.0 | 1.0 | 1.0 | 1.0 | 1.0 | 1.0 |
| Arylpon ® F<br>Laureth-2 | — | — | 1.5 | — | — | — | — | — | — | — |

TABLE 3-continued

Cosmetic preparations (water, preservative to 100% by weight)

| | | | | | | | | | | |
|---|---|---|---|---|---|---|---|---|---|---|
| Magnesium Sulfate Hepta Hydrate | — | — | — | — | — | — | — | — | 1.0 | 1.0 |
| Glycerin (86% by weight) | — | — | — | — | — | 3.0 | 3.0 | 2.0 | 5.0 | 5.0 |

| Composition (INCI) | 41 | 42 | 43 | 44 | 45 | 46 | 47 | 48 | 49 | 50 |
|---|---|---|---|---|---|---|---|---|---|---|
| Dehymuls ® PGPH<br>Polyglyceryl-2 Dipolyhydroxystearate | 2.0 | 3.0 | — | 5.0 | — | — | — | — | — | — |
| Lameform ® TGI<br>Polyglycerol-3 Diiosostearate | 4.0 | 1.0 | — | — | — | — | — | — | — | — |
| Emulgade ® PL 68/50<br>Cetearyl Glucoside (and) Cetearyl Alcohol | — | — | — | — | 4.0 | — | — | — | 3.0 | — |
| Dehyquart C 4043<br>Dipalmitoylethyl Hydroxyethylmonium Methosulfate (and) Ceteareth-20 | 2.0 | 2.0 | 2.0 | 2.0 | 2.0 | 2.0 | 2.0 | 2.0 | 2.0 | 2.0 |
| Tegocare ® PS<br>Polyglyceryl-3 Methylglucose Distearate | — | — | — | — | — | — | 4.0 | — | — | — |
| Eumulgin VL 75<br>Polyglyceryl-2 Dipolyhydroxystearate (and) Lauryl Glucosde (and) Glycerin | — | — | — | — | — | 3.5 | — | — | 2.5 | — |
| Bees Wax | 3.0 | 2.0 | 5.0 | 2.0 | — | — | — | — | — | — |
| Cutina ® GMS<br>Glyceryl Stearate | — | — | — | — | — | 2.0 | 4.0 | — | — | 4.0 |
| Lanette ® O<br>Cetearyl Alcohol | — | — | 2.0 | — | 2.0 | 4.0 | 2.0 | 4.0 | 4.0 | 1.0 |
| Antaron ® V 216<br>PVP/Hexadecene Copolymr | — | — | — | — | — | 3.0 | — | — | — | 2.0 |
| Plantaren ® 818<br>Cocoglycerides | 5.0 | — | 10.0 | — | 8.0 | 6.0 | 6.0 | — | 5.0 | 5.0 |
| Finsolv ® TN<br>C12/15 Alkyl Benzoate | — | 6.0 | — | 2.0 | — | — | 3.0 | — | — | 2.0 |
| Cetiol ® J 600<br>Oleyl Erucate | 2.0 | — | 3.0 | 5.0 | 4.0 | 3.0 | 3.0 | — | 5.0 | 4.0 |
| Cetiol ® OE<br>Dicaprylyl Ether | 3.0 | — | — | — | 1.0 | — | — | — | — | — |
| Mineral Oil | — | 4.0 | — | 4.0 | — | 2.0 | — | 1.0 | — | — |
| Cetiol ® PGL<br>Hexadecanol (and) Hexyldecyl Laurate | — | 7.0 | 3.0 | 7.0 | 4.0 | — | — | — | 1.0 | — |
| Panthenol/Bisabolol | 1.2 | 1.2 | 1.2 | 1.2 | 1.2 | 1.2 | 1.2 | 1.2 | 1.2 | 1.2 |
| Aloe Vera Gel Concentrate<br>Aloe Barbadensis (and) Citric Acid (and) Ascorbic Acid | 1.0 | 1.0 | 1.0 | 1.0 | 1.0 | 1.0 | 1.0 | 1.0 | 1.0 | 1.0 |
| Copherol ® F 1300<br>Tocopherol/Tocopheyl Acetate | 0.5 | 1.0 | 1.0 | 2.0 | 1.0 | 1.0 | 1.0 | 2.0 | 0.5 | 2.0 |
| Neo Heliopan ® Hydro<br>Sodium Phenylbenzimidazole Sulfonate | 3.0 | — | — | 3.0 | — | — | 2.0 | — | 2.0 | — |
| Neo Heliopan ® 303<br>Octocrylene | — | 5.0 | — | — | — | 4.0 | 5.0 | — | — | 10.0 |
| Neo Heliopan ® BB<br>Benzophenone-3 | 1.5 | — | — | 2.0 | 1.5 | — | — | — | 2.0 | — |
| Neo Heliopan ® E 1000<br>Isoamyl p-Methoxycinnamate | 5.0 | — | 4.0 | — | 2.0 | 2.0 | 4.0 | 10.0 | — | — |
| Neo Heliopan ® AV<br>Octyl Methoxycinnamate | 4.0 | — | 4.0 | 3.0 | 2.0 | 3.0 | 4.0 | — | 10.0 | 2.0 |
| Uvinol ® T 150<br>Octyl Triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium Dioxide | — | 2.0 | 2.0 | — | — | — | — | 5.0 | — | — |
| Glycerin (86% by weight) | 5.0 | 5.0 | 5.0 | 5.0 | 5.0 | 5.0 | 5.0 | 5.0 | 5.0 | 5.0 |

(1–4) hair rinse, (5–6) hair conditioner, (7–8) shower bath, (9) shower gel, (10) wash lotion, (11–14) "2-in-1 shower bath", (15–20) shampoo, (21–25) foam bath, (26) soft cream, (27, 28) moisturizing emulsion, (29, 30 night cream), (41) w/o sun cream, (42–44) w/o sun lotion, (45, 48, 50) o/w sun lotion, (46, 47, 49) o/w sun cream.

What is claimed is:

1. A cleaning composition comprising:
   (a) an esterquat; and
   (b) aloe.

2. The composition of claim 1 wherein the esterquat is present in the composition in an amount of from about 1 to 50% by weight, based on the weight of the composition.

3. The composition of claim 1 wherein the aloe is present in the composition in an amount of from about 1 to 10% by weight, based on the weight of the composition.

4. The composition of claim 1 wherein the aloe is aloe vera.

5. The composition of claim 1 further comprising a surfactant selected from the group consisting of an anionic surfactant, a nonionic surfactant, a cationic surfactant, an amphoteric surfactant, a zwitterionic surfactant, and mixtures thereof.

6. The composition of claim 5 wherein the surfactant is present in the composition in an amount of from about 1 to 25% by weight, based on the weight of the composition.

7. A laundry detergent composition containing the cleaning composition of claim 1.

8. A skin-care composition containing the cleaning composition of claim 1.

9. A hair care composition containing the cleaning composition of claim 1.

10. A dishwashing composition containing the cleaning composition of claim 1.

11. A process for cleaning a substrate comprising contacting the substrate with a cleaning composition containing:
 (a) an esterquat; and
 (b) aloe, wherein the substrate is selected from the group consisting of textile fibers, human skin, and hair.

12. The process of claim 11 wherein the esterquat is present in the composition in an amount of from about 1 to 50% by weight, based on the weight of the composition.

13. The process of claim 11 wherein the aloe is present in the composition in an amount of from about 1 to 10% by weight, based on the weight of the composition.

14. The process of claim 11 wherein the aloe is aloe vera.

15. The process of claim 11 wherein the composition further comprises a surfactant selected from the group consisting of an anionic surfactant, a nonionic surfactant, a cationic surfactant, an amphoteric surfactant, a zwitterionic surfactant, and mixtures thereof.

16. The process of claim 15 wherein the surfactant is present in the composition in an amount of from about 1 to 25% by weight, based on the weight of the composition.

* * * * *